United States Patent [19]

Andree et al.

[11] Patent Number: 6,107,252
[45] Date of Patent: Aug. 22, 2000

[54] SUBSTITUTED PHENYL URACILS AND THEIR USE AS HERBICIDES

[75] Inventors: Roland Andree; Mark Wilhelm Drewes, both of Langenfeld, Germany; Markus Dollinger, Overland Park, Kans.

[73] Assignee: Bayer Aktiengesellschaft, Leverkusen, Germany

[21] Appl. No.: 09/194,151

[22] PCT Filed: Apr. 21, 1997

[86] PCT No.: PCT/EP97/01998

§ 371 Date: Oct. 23, 1998

§ 102(e) Date: Oct. 23, 1998

[87] PCT Pub. No.: WO97/42176

PCT Pub. Date: Nov. 13, 1997

[30] Foreign Application Priority Data

May 2, 1996 [DE] Germany ............... 196 17 532

[51] Int. Cl.⁷ ............... C07D 239/54; A01N 40/54
[52] U.S. Cl. ............... 504/243; 544/311
[58] Field of Search ............... 504/243; 544/311

[56] References Cited

U.S. PATENT DOCUMENTS

| | | | |
|---|---|---|---|
| 5,169,430 | 12/1992 | Strunk et al. | 71/92 |
| 5,486,661 | 1/1996 | Strunk et al. | 544/311 |
| 5,593,945 | 1/1997 | Andree et al. | 504/243 |
| 5,641,725 | 6/1997 | Goto et al. | 504/134 |
| 5,681,794 | 10/1997 | Andree et al. | 504/234 |
| 5,700,805 | 12/1997 | Schäfer et al. | 514/269 |

FOREIGN PATENT DOCUMENTS

| | | |
|---|---|---|
| 93/11669 | 6/1993 | WIPO . |
| 97/05117 | 2/1997 | WIPO . |

Primary Examiner—Mukund J. Shah
Assistant Examiner—Deepak R. Rao
Attorney, Agent, or Firm—Joseph C. Gil; Carol Marmo

[57] ABSTRACT

The invention relates to novel substituted phenyluracils of the general formula (I)

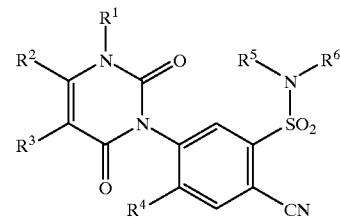

(I)

in which $R^1$, $R^2$, $R^3$, $R^4$, $R^5$ and $R^6$ are each as defined in the description, to a process for preparing the novel substances and to their use as herbicides. Furthermore, the invention relates to novel substituted chlorophenyluracils of the formula

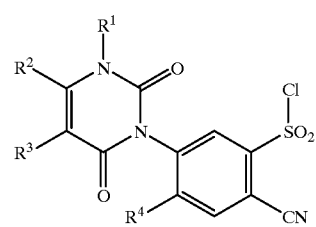

(II)

in which $R^1$, $R^2$, $R^3$ and $R^4$ are each as defined in the description, and to a process for preparing these substances.

6 Claims, No Drawings

SUBSTITUTED PHENYL URACILS AND THEIR USE AS HERBICIDES

This application is a 371 of PCT/EP97/01998 filed Apr. 21, 1997.

The invention relates to novel substituted phenyluracils, to a process for their preparation and to their use as herbicides.

It is known that certain substituted phenyluracils, such as, for example, the compound 1-(4-chloro-5-dimethylaminosulfonyl-2-fluoro-phenyl)-3,6-dihydro-2,6-dioxo-4-trifluoromethyl-1(2H)pyrimidine, have herbicidal properties (cf. U.S. Pat. No. 5,169,430). However, the herbicidal activity of these compounds and their compatibility with crop plants is not always entirely satisfactory.

It is an object of the present invention to provided novel phenyluracils having optimized herbicidal activity and at the same time compatibility with crop plants. This invention, accordingly, provides novel substituted phenyluracils of the general formula (I)

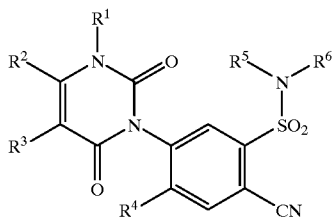

(I)

in which

- $R^1$ represents hydrogen, formyl or optionally substituted alkyl,
- $R^2$ represents optionally substituted alkyl,
- $R^3$ represents hydrogen, halogen or optionally substituted alkyl,
- $R^4$ represents hydrogen, cyano, nitro, halogen or alkoxy,
- $R^5$ represents hydrogen, hydroxyl, amino or represents alkyl, alkoxy, alkylamino, dialkylamino, alkylcarbonyl, alkylcarbonylamino, alkoxycarbonyl, alkylsulphonyl, alkylsulphonylamino, alkenyl, alkenyloxy, alkinyl, cycloalkyl, cycloalkylalkyl, aryl, arylamino, arylcarbonylamino, arylsulphonylamino, arylalkyl, heterocyclyl or heterocyclylalkyl, each of which is optionally substituted, and
- $R^6$ represents hydrogen or represents alkyl, alkenyl or alkinyl, each of which is optionally substituted, or together with $R^5$ represents an alkanediyl group which optionally contains an oxygen atom at the beginning or the end or within the hydrocarbon chain.

The novel substituted phenyluracils of the general formula (I) are obtained when chlorosulphonylphenyluracils of the general formula (II)

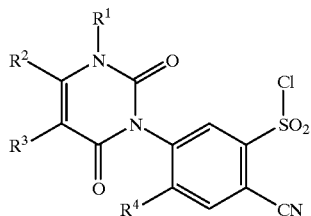

(II)

in which $R^1$, $R^2$, $R^3$ and $R^4$ are each as defined above, are reacted with amino compounds of the general formula (III)

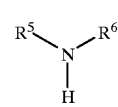

(III)

in which $R^5$ and $R^6$ are each as defined above, if appropriate in the presence of a reaction auxiliary and if appropriate in the presence of a diluent.

The novel substituted phenyluracils of the general formula (I) have strong herbicidal activity. Surprisingly, the novel compounds of the formula (I) are significantly more compatible with crop plants, such as, for example, wheat or barley, and have considerably higher activity against weeds.

The invention preferably provided compounds of the formula (I) in which

- $R^1$ represents hydrogen, formyl or optionally cyano-, halogen- or $C_1$–$C_4$-alkoxy-substituted alkyl having 1 to 6 carbon atoms,
- $R^2$ represents optionally halogen-substituted alkyl having 1 to 6 halogen atoms,
- $R^3$ represents hydrogen, halogen or optionally halogen-substituted alkyl having 1 to 6 carbon atoms,
- $R^4$ represents hydrogen, cyano, nitro, halogen or alkoxy having 1 to 4 carbon atoms,
- $R^5$ represents hydrogen, hydroxyl, amino or represents alkyl, alkoxy, alkylamino, dialkylamino, alkylcarbonyl, alkylcarbonylamino, alkoxycarbonyl, alkylsulphonyl or alkylsulphonylamino having in each case up to 6 carbon atoms and being in each case optionally substituted by cyano, halogen or $C_1$–$C_4$-alkoxy, represents alkenyl, alkenyloxy or alkinyl having in each case up to 6 carbon atoms and being in each case optionally substituted by halogen, represents cycloalkyl or cycloalkylalkyl having 3 to 6 carbon atoms in the cycloalkyl group and optionally up to 4 carbon atoms in the alkyl moiety and being in each case optionally substituted by cyano, halogen or $C_1$–$C_4$-alkyl, represents aryl, arylamino, arylcarbonylamino, arylsulphonylamino or arylalkyl having 6 to 10 carbon atoms in the aryl group and optionally up to 4 carbon atoms in the alkyl moiety and being in each case optionally substituted by cyano, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl or $C_1$–$C_4$-alkylsulphonyl, or represents heterocyclyl or heterocyclylalkyl, in each case optionally substituted by cyano, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl or $C_1$–$C_4$-alkylsulphonyl, the heterocyclyl group being selected from the group consisting of furyl, tetrahydrofuryl, thienyl, tetrahydrothienyl, oxazolyl, isoxazolyl, thiazolyl, oxadiazolyl, thiadiazolyl, pyrazolyl, pyridinyl, pyrimidinyl, triazinyl, indolyl, quinolinyl, quinoxalinyl and the alkyl moiety optionally containing up to 4 carbon atoms, and $R^6$ represents hydrogen or represents alkyl, alkenyl or alkinyl having in each case up to 6 carbon atoms and being in each case optionally substituted by halogen, or together with $R^5$ represents an alkanediyl group having up to 6 carbon atoms which optionally contains an oxygen atom at the beginning or the end or within the hydrocarbon chain.

The saturated or unsaturated hydrocarbon chains in the definitions, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention in particular relates to compounds of the formula (I) in which $R^1$ represents hydrogen or represents methyl, ethyl, n- or i-propyl, n-, i-, s- or t-butyl, each of which is optionally substituted by cyano, fluorine, chlorine, methoxy or ethoxy, $R^2$ represents methyl or ethyl, each of which is optionally substituted by fluorine and/or chlorine, $R^3$ represents hydrogen, fluorine, chlorine, bromine or represents methyl or ethyl, each of which is optionally substituted by fluorine and/or chlorine, $R^4$ represents hydrogen, cyano, nitro, fluorine, chlorine or methoxy, $R^5$ represents hydrogen, hydroxyl, amino or represents methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, acetyl, propionyl, n- or i-butyroyl, acetylamino, propionylamino, methoxycarbonyl, ethoxycarbonyl, methylsulphonyl, ethylsulphonyl, n- or i-propylsulphonyl, n-, i-, s- or t-butylsulphonyl, methylsulphonylamino, ethylsulphonylamino, n- or i-propylsulphonylamino, n-, i-, s- or t-butylsulphonylamino, each of which is optionally substituted by cyano, fluorine, chlorine, methoxy or ethoxy, represents propenyl, butenyl, propenyloxy, butenyloxy, propinyl or butinyl, each of which is optionally substituted by fluorine, chlorine and/or bromine, represents cyclopropyl, cyclobutyl, cyclopentyl, cyclohexyl, cyclopropylmethyl, cyclobutylmethyl, cyclopentylmethyl or cyclohexylmethyl, each of which is optionally substituted by cyano, fluorine, chlorine, bromine, methyl or ethyl, represents phenyl, phenylamino, phenylcarbonylamino, phenylsulphonylamino, benzyl or phenylethyl, each of which is optionally substituted by cyano, fluorine, chlorine, bromine, methyl, ethyl, n- or i-propyl, n-, i-, s- or t-butyl, difluoromethyl, trifluoromethyl, methoxy, ethoxy, n- or i-propoxy, difluoromethoxy, trifluoromethoxy, methylthio, ethylthio, difluoromethylthio, trifluoromethylthio, methylsulphinyl, ethylsulphinyl, methylsulphonyl or ethylsulphonyl, and $R^6$ represents hydrogen or represents methyl, ethyl, n- or i-propyl, propenyl, butenyl, propinyl or butinyl, each of which is optionally substituted by fluorine or chlorine, or together with $R^5$ represents ethane-1,2-diyl (dimethylene), propane-1,3-diyl (trimethylene), 2-oxa-propane-1,3-diyl, butane-1,4-diyl (tetramethylene), pentane-1,5-diyl or 3-oxa-pentane-1,5-diyl.

The general or preferred radical definitions listed above apply both to the end products of the formula (I) and, correspondingly, to the starting materials and/or intermediates which are required in each case for the preparation. These radical definitions can be combined with each other at will, i.e. combinations between the given preferred ranges are also possible.

Examples of compounds of the formula (I) according to the invention are listed in the groups below.

Group 1

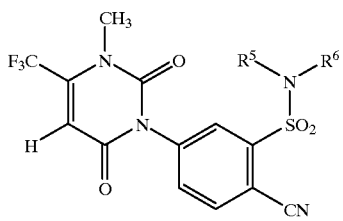

Here, group $NR^5R^6$ has, for example, the meanings given in the list below: amino, hydroxylamino, hydrazino, methylamino, ethylamino, n-propylamino, i-propylamino, n-butylamino, i-butylamino, s-butylamino, t-butylamino, dimethylamino, diethylamino, dipropylamino, 2-cyano-ethylamino, 2-methoxy-ethylamino, 2-ethoxy-ethylamino, methoxyamino, ethoxyamino, n-propoxyamino, i-propoxyamino, n-butoxyamino, i-butoxyamino, s-butoxyamino, 1-methyl-hydrazino, 2-methyl-hydrazino, 2-ethyl-hydrazino, 2-n-propyl-hydrazino, 2-i-propylhydrazino, 2-n-butyl-hydrazino, 2-i-butyl-hydrazino-2-s-butyl-hydrazino, 2-t-butyl-hydrazino, 2,2-dimethyl-hydrazino, acetylamino, propionylamino, 2-acetyl-hydrazino, 2-propionyl-hydrazino, 2-methylsulphonyl-hydrazino, 2-ethylsulphonyl-hydrazino, allylamino, propargylamino, allyloxyamino, N-methyl-methoxyamino, cyclopropylamino, cyclobutylamino, cyclopentylamino, cyclohexylamino, cyclopropylmethylamino, cyclobutylmethylamino, cyclopentylamino, cyclohexylmethylamino, phenylamino, 2-fluoro-, 3-fluoro-, 4-fluoro-, 2-chloro-, 3-chloro-, 4-chlor-, 2-methyl-, 3-methyl-, 4-methyl-, 2-trifluoromethyl-, 3-trifluoromethyl-, 4-trifluoromethyl-, 2-methoxy-, 3-methoxy-, 4-methoxy-, 2-difluoromethoxy-, 4-difluoromethoxy-, 2-trifluoromethoxy-, 4-trifluoromethoxy-, 4-methylthio-, 4-methylsulphinyl- and 4-methylsulphonyl-phenyl-amino, phenylhydrazino, 2-fluoro-, 3-fluoro-, 4-fluoro-, 2-chloro-, 3-chloro,- 4-chloro-, 2-methyl-, 3-methyl-, 4-methyl-, 2-trifluoromethyl-, 3-trifluoromethyl-, 4-trifluoromethyl-, 2-methoxy, 3-methoxy-, 4-methoxy-, 2-difluoromethoxy-4-difluoromethoxy-, 2-trifluoromethoxy-, 4-trifluoromethoxy-phenylhydrazino, phenylcarbonylhydrazino, phenylsulfonylhydrazino, 2-fluoro-, 3-fluoro-, 4-fluoro-, 2-chloro-, 3-chloro-, 4-chloro-, 2-methyl-, 3-methyl-, 4-methyl-, 2-trifluoromethyl-, 3-trifluoromethyl-, 4-trifluoromethyl-, 2-methoxy-, 3-methoxy-, 4-methoxy-, 2-difluoromethoxy-, 4-difluoromethoxy-, 2-trifluoromethoxy-, 2-trifluoromethoxy-, 4-trifluoromethoxy-phenylsulphonylhydrazino, benzylamino, 2-fluoro-, 3-fluoro-, 4fluoro-, 2-chloro-, 3-chloro-, 4-chloro-, 2-methyl-, 3-methyl-, 4-methyl-, 2-trifluoromethyl-, 3-trifluoromethyl-, 4-trifluoromethyl-, 2-methoxy-, 3-methoxy-, 4-methoxy-, 2-difluoromethoxy-, 4-difluoromethoxy-, 2-trifluoromethoxy-, 4-trifluoromethoxy-benzylamino, 1-phenylethylamino, 2-phenyl-ethylamino, aziridino, pyrrolidino, piperidino, morpholino.

Group 2

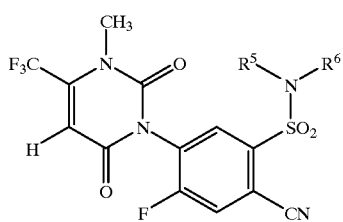

Here, the group NR$^5$R$^6$ has, for example, the meanings given above in Group 1.

Group 3

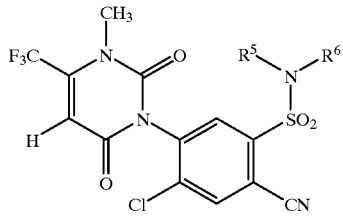

Here, the group NR$^5$R$^6$ has, for example, the meanings given above in Group 1.

Group 4

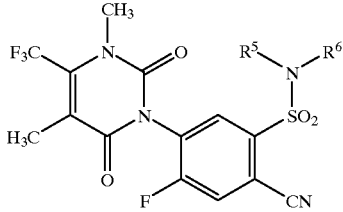

Here, the group NR$^5$R$^6$ has, for example, the meanings given above in Group 1.

Group 5

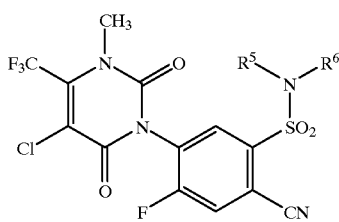

Here, the group NR$^5$R$^6$ has, for example, the meanings given above in Group 1.

Group 6

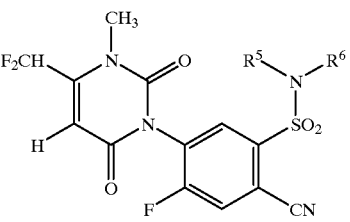

Here, the group NR$^5$R$^6$ has, for example, the meanings given above in Group 1.

Group 7

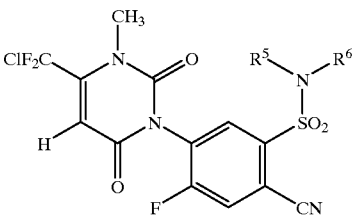

Here, the group NR$^5$R$^6$ has, for example, the meanings given above in Group 1.

Group 8

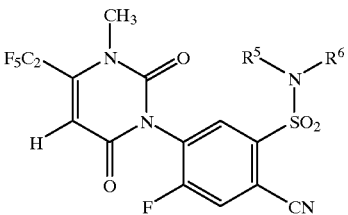

Here, the group NR$^5$R$^6$ has, for example, the meanings given above in Group 1.

Using, for example, 1-(3-chlorosulphonyl-4-cyano-phenyl)-3,6-dihydro-2,6-dioxo-3-methyl-4-trifluoromethyl-2(2H)-pyrimidine and aniline as starting materials, the course of the reaction in the process according to the invention can be illustrated by the following equation:

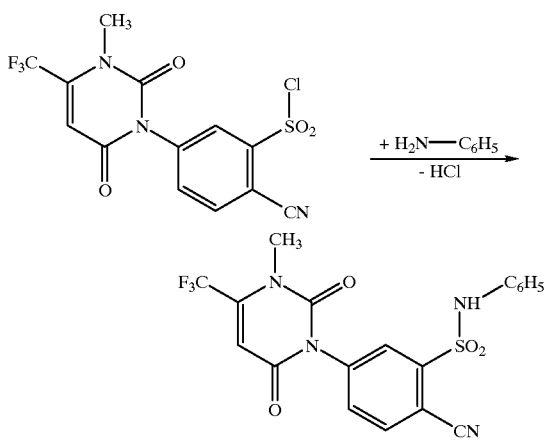

The formula (II) provides a general definition of the chlorosulphonylphenyluracils to be used as starting materials in the process according to the invention for preparing compounds of the formula (I). In the formula (II), $R^1$, $R^2$, $R^3$ and $R^4$ each preferably or in particular have those meanings which have already been mentioned above, in connection with the description of the compounds of the formula (I) according to the invention, as being preferred or as being particularly preferred for $R^1$, $R^2$, $R^3$ and $R^4$.

The starting materials of the formula (I) have hitherto not been disclosed in the literature; as novel substances, they also form part of the subject matter of the present application.

The novel chlorosulphonylphenyluracils of the formula (II) are obtained when appropriate aminophenyluracils of the general formula (IV)

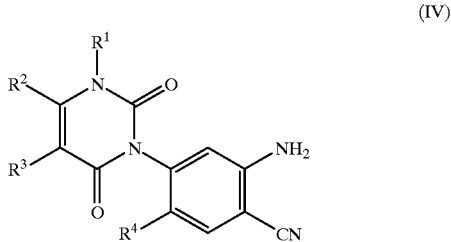

in which $R^1$, $R^2$, $R^3$ and $R^4$ are each as defined as above, are reacted with an alkali metal nitrite, such as, for example, sodium nitrite, in the presence of hydrochloric acid and, if appropriate, in the presence of an organic diluent, such as, for example, acetic acid, at temperatures between −10° C. and +10° C., and the resulting diazonium salt solution is reacted with sulphur dioxide in the presence of a diluent, such as, for example, dichloromethane, 1,2-dichloroethane or acetic acid, and in the presence of a catalyst, such as, for example, copper(I) chloride and/or copper(II) chloride, at temperatures between −10° C. and +50° C. (cf. the Preparation Examples).

The aminophenyluracils of the general formula (IV) required as intermediates are known and/or can be prepared by known processes (cf. EP 648749, Preparation Examples).

The formula (III) provides a general definition of the amino compounds further to be used as starting materials in the process according to the invention. In the formula (III), $R^5$ and $R^6$ each preferably or in particular have those meanings which have already been mentioned above, in connection with the description of the compounds of the formula (I) according to the invention, as being preferred or as being particularly preferred for $R^5$ and $R^6$.

The starting materials of the formula (III) are known chemicals for synthesis.

Suitable reaction auxiliaries for the process according to the invention for preparing the compounds of the formula (I) are generally the customary inorganic or organic bases or acid acceptors. These include preferably alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or i-propoxide, n-, i-, s- or t-butoxide; furthermore also basic organic nitrogen compounds, such as, for example, trimethylamine, N,N-dimethylcyclohexylamine, tributylamine, ethyl-diisopropylamine, N,N-dimethylcyclohexylamine, dicyclohexylamine, ethyl-dicyclohexylamine, N,N-dimethylaniline, N,N-dimethylbenzylamine, pyridine, 2-methyl-, 3-methyl-, 4-methyl, 2,4-dimethyl-, 2,6-dimethyl-, 3,4-dimethyl- and 3,5-dimethylpyridine, 5-ethyl-2-methyl-pyridine, 4-dimethylamino-pyridine, N-methyl-piperidine, 1,4-diazabicyclo[2,2,2]-octane, (DABCO), 1,5-diazabicyclo[4,3,0]-non-5-ene (DBN), or 1,8-diazabicyclo[5,4,0]-undec-7-ene (DBU).

Suitable diluents for carrying out the process according to the invention are above all inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxan, tetrahydrofuran or ethylene glycol dimethyl ether or ethylene glycol diethyl ether; ketones, such as acetone, butanone or methyl isobutyl ketone, nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide, esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the process according to the invention, the reaction temperatures can be varied over a relatively wide range. In general, temperatures of between 0° C. and 150° C., preferably between 10° C. and 120° C., are employed.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are employed in approximately equimolar amounts. However, it is also possible to use one of the components in a relatively large excess. The reaction is generally carried out in a suitable solvent in the presence of a reaction auxiliary, and the reaction mixture is generally stirred for several hours at the temperature required Work-up is carried out according to customary methods (cf. the Preparation Examples).

The active compounds according to the invention can be used as defoliants, desiccants, haulm-killer and, especially, as weed-killers. Weeds, in the broadest sense, are all plants which grow in locations where they are undesired. Whether the compounds according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weed of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyledonous weeds in monocotyledonous crops, such as, for example, maize, wheat and barley, both by the pre- and post-emergence method.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine encapsulations in polymeric substances.

These formulations are produced in a known-manner, for example by mixing the active compounds with extenders, that is liquid solvents and/or solid carriers, optionally with the use of surfactants, that is emulsifiers and/or dispersants and/or foam-formers.

If the extender used is water, it is also possible to employ for example organic solvents such as auxiliary solvents. Essentially, suitable liquid solvents include: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable rock carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylen fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be used as such or, in their formulations, also as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

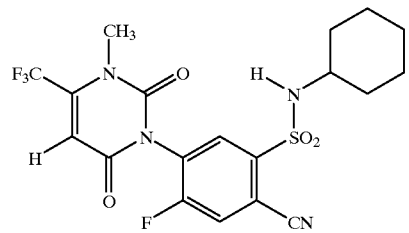

At room temperature (approximately 20° C.), a solution of 2.5 g (6.1 mmol) of 1-(5-chlorosulphonyl-4-cyano-5-fluoro-phenyl)-3,6-dihydro-2,6-dioxo-3-methyl-4-trifloromethyl-1-(2H)-pyrimidine in 20 ml of methylene chloride is added dropwise and with stirring to a mixture of 0.6 g (6.1 mmol) of cyclohexylamine, 0.6 g (6.1 mmol) of pyridine and 30 ml of methylene chloride, and the mixture is then stirred at room temperature for a further two days approximately. The mixture is then diluted to about twice its volume with 1N hydrochloric acid, and the organic phase is separated off, washed with water, dried with sodium sulphate and filtered. The filtrate is concentrated under water pump vacuum and the residue is purified by column chromatography (ethyl acetate/chloroform, vol.: 1/1, silica gel).

This gives 1.1 g (38% of theory) of 1-(5-cyclohexylaminosulfonyl-4-cyano-5-fluoro-phenyl)-3,6-dihydro-2,6-dioxo-3-methyl-4-trifluoromethyl-1-(2H) pyrimidine of melting point 167° C.

By the method of Preparation Example 1 and in accordance with the general description of the preparation process according to the invention it is also possible to prepare, for example, the compounds of the formula (I) listed in Table 1 below.

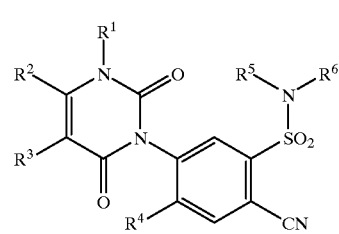

TABLE 1

Examples of compounds of the formula (I)

| Ex. No. | $R^1$ | $R^2$ | $R^3$ | $R^4$ | $R^5$ | $R^6$ | Melting point (°C.) |
|---|---|---|---|---|---|---|---|
| 2 | $CH_3$ | $CF_3$ | H | F | H | $C_2H_5$ | 188 |
| 3 | $CH_3$ | $CF_3$ | H | F | H | $i$-$C_3H_7$ | $^1$H NMR ($CDCl_3$, d): 6.39 ppm (s) |
| 4 | $CH_3$ | $CF_3$ | H | F | $CH_3$ | $CH_3$ | |
| 5 | $CH_3$ | $CF_3$ | H | F | $CH_3$ | $CH_2H_5$ | |
| 6 | $CH_3$ | $CF_3$ | H | F | $CH_3$ | $i$-$C_3H_7$ | |
| 7 | $CH_3$ | $CF_3$ | H | F | H | $OCH_3$ | |
| 8 | $CH_3$ | $CF_3$ | H | F | $CH_3$ | $OCH_3$ | |
| 9 | $CH_3$ | $CF_3$ | H | F | $CH_3$ | $CH_2OC_4H_9$ | |
| 10 | $CH_3$ | $CF_3$ | H | F | $CH_3$ | $CH_2SC_4H_9$ | |
| 11 | $CH_3$ | $CF_3$ | H | F | $CH_3$ | $CH_2C_6H_5$ | |
| 12 | $CH_3$ | $CF_3$ | H | F | $CH_3$ | $CH_2CH\!=\!CH_2$ | |
| 13 | $CH_3$ | $CF_3$ | H | F | $CH_3$ | $CH_2C\!\equiv\!CH$ | |
| 14 | $CH_3$ | $CF_3$ | H | F | $CH_3$ | $CH_2CN$ | |
| 15 | $CH_3$ | $CF_3$ | H | F | $CH_3$ | $CH_2CH_2OH$ | |
| 16 | $CH_3$ | $CH_3$ | H | F | H | $NHN(CH_3)_2$ | |
| 17 | $CH_3$ | $CF_3$ | H | F | —$(CH_2)_2$—O—$(CH_2)_2$— | | 200 |

Starting materials of the formula (II):

Example (II-1)

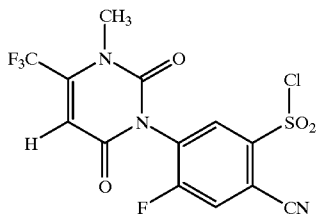

A solution of 0.42 g of sodium nitrite in 1.2 ml of water is added dropwise with stirring to a mixture of 2.0 g (6.1 mmol) of 1-(5-amino-4-cyano-5-fluoro-phenyl)-3,6-dihydro-2,6-dioxo-3-methyl-4-trifluoromethyl-1-(2H)-pyrimidine, 3.5 ml of conc. hydrochloric acid and 2 ml of acetic acid which had been cooled to 0° C. to 5° C. The mixture is stirred at 0° C. to 5° C. for approximately 30 minutes and then added dropwise to a mixture of 2.5 ml of sulphur dioxide, 1.2 g of copper(II) chloride and 6.5 ml of acetic acid which had also been cooled to 0° C. to 5° C. The resulting mixture is stirred at room temperature (approximately 20° C.) for about 15 hours and then poured onto ice-water. The resulting crystalline product is isolated by filtration with suction.

This gives 1.1 g (42% of theory) of 1-(5-chlorosulphonyl-4-cyano-5-fluorophenyl)-3,6-dihydro-2,6-dioxo-3-methyl-4-trifluoromethyl-1(2H)-pyrimidine.

Starting materials of the formula (IV):

Example (IV-1)

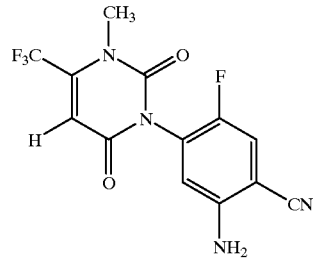

0.17 g (1.2 mmol) of pivaloyl chloride are added with stirring to a mixture of 0.50 g (1.2 mmol) of 1-(4-cyano-2-fluoro-5-trifluoroacetylamino-phenyl)-3,6-dihydro-2,6-dioxo-3-methyl-4-trifluoromethyl-1-(2H)-pyrimidine, 1 ml of triethylamine and 50 ml of acetonitrile, and the reaction mixture is stirred at 20° C. for 18 hours and at 60° C. for a further 15 hours. The mixture is then concentrated under water pump vacuum, the residue is shaken with 1N hydrochloric acid/ethyl acetate and the organic phase is separated off, dried with sodium sulphate and filtered. The filtrate is concentrated under water pump vacuum and the residue is worked up by column chromatography (silica gel, chloroform/ethyl acetate, vol.: 1:1).

In addition to unreacted 1-(4-cyano-2-fluoro-5-trifluoroacetylamino-phenyl)-3,6-dihydro-2,6-dioxo-3-methyl-4-trifluoromethyl-1-(2H)pyrimidine (first fraction: 0.30 g), 0.2 g (50% of theory) of 1-(4-cyano-2-fluoro-5-amino-phenyl)-3,6-dihydro-2,6-dioxo-3-methyl-4-trifluoromethyl-1-(2H)-pyrimidine are obtained as second fraction.

Melting point: 195° C.

Use Examples

In the use examples, the following compound is used as comparative substance:

(A)

1-(4-Chloro-5-dimethylaminosulphonyl-2-fluoro-phenyl)-3,6-dihydro-2,6-dioxo-4-trifluoromethyl-1(2H)-pyrimidine (known from U.S. Pat. No. 5,169,430).

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After approximately 24 hours, the soil is watered with the preparation of the active compound. It is advantageous to keep the amount of water per unit area constant. The concentration of the active compound in the preparation is immaterial, only the amount of active compound applied per unit area matters.

After three weeks, the degree of damage to the plants is rated in % damage by comparison with the development of the untreated control.

The figures denote:

0%=no effect (like untreated control)

100%=total destruction

In this test, at an application rate of 30 and 60 g/ha, respectively, for example the compound of Preparation Example 4 shows considerably stronger activity than the known compound (A) against weeds such as Datura (100%), Ipomoea (100%), Polygonum (100%), Echinochlea (70%), Sorghum (100%) and Xanthium (95%), and is well tolerated by crop plants, such as, for example, maize (0%), wheat (0%) and barley (0%).

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular desired amounts of active compound are applied in 1000 l of water/ha.

After three weeks, the degree of damage to the plants is rated in % damage in comparison with the development of the untreated control.

The figure denotes:

0%=no effect (like untreated control)

100%=total destruction

In this test, at an application rate of 30 g/ha, for example the compounds of Preparation Examples 1 and 4 show considerably stronger activity than the known compound (A) against weeds such as Amaranthus (100%), Chenopodium (100%), Stellaria (90%), Veronica (95%–100%) and Viola (90%–95%), and they are well tolerated by crop plants, such as, for example, barley (20%).

What is claimed is:

1. A substituted phenyluracil of the general formula (I)

(I)

wherein $R^1$ represents hydrogen, formyl or unsubstituted or cyano-, halogen- or $C_1$–$C_4$-alkoxy-substituted alkyl having 1 to 6 carbon atoms, $R^2$ represents unsubstituted or halogen-substituted alkyl having 1 to 6 carbon atoms, $R^3$ represents hydrogen, halogen or unsubstituted or halogen-substituted alkyl having 1 to 6 carbon atoms, $R^4$ represents hydrogen, cyano, nitro, halogen or alkoxy having 1 to 4 carbon atoms, $R^5$ represents hydrogen, hydroxyl, amino or represents alkyl, alkoxy, alkylamino, dialkylamino, alkylcarbonyl, alkylcarbonylamino, alkoxycarbonyl, alkylsulphonyl or alkylsulphonylamino having in each case up to 6 carbon atoms and being in each case unsubstituted or substituted by cyano, halogen or $C_1$–$C_4$-alkoxy, represents alkenyl, alkenyloxy or alkynyl having in each case up to 6 carbon atoms and being in each case unsubstituted or substituted by halogen, represents cycloalkyl or cycloalkylalkyl having 3 to 6 carbon atoms in the cycloalkyl group and up to 4 carbon atoms in the alkyl moiety and being in each case unsubstituted or substituted by cyano, halogen or $C_1$–$C_4$-alkyl, represents aryl, arylamino, arylcarbonylamino, arylsulphonylamino or arylalkyl having 6 to 10 carbon atoms in the aryl group and up to 4 carbon atoms in the alkyl moiety and being in each case unsubstituted or substituted by cyano, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl or $C_1$–$C_4$-alkylsulphonyl, or represents heterocyclyl or heterocyclylalkyl, in each case unsubstituted or substituted by cyano, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl or $C_1$–$C_4$-alkylsulphonyl, the heterocyclyl group being selected from the group consisting of furyl, tetrahydrofuryl, thienyl, tetrahydrothienyl, oxazolyl, isoxazolyl, thiazolyl, oxadiazolyl, thiadiazolyl, pyrazolyl, pyridinyl, pyrimidinyl, triazinyl, indolyl, quinolinyl, quinoxalinyl and the alkyl moiety containing up to 4 carbon atoms, and $R^6$ represents hydrogen or represents alkyl, alkenyl or alkynyl having in each case up to 6 carbon atoms and being in each case unsubstituted or substituted by halogen, or together with $R^5$ represents an alkanediyl group having up to 6 carbon atoms which contains zero or one oxygen atom at the beginning or the end or within the hydrocarbon chain.

2. A substituted phenyluracil of the general formula (I) according to claim 1, wherein $R^1$ represents hydrogen or represents methyl, ethyl, n- or i-propyl, n-, i-, s- or t-butyl, each of which is unsubstituted or substituted by cyano, fluorine, chlorine, methoxy or ethoxy, $R^2$ represents methyl or ethyl, each of which is unsubstituted or substituted by a halogen selected from the group consisting of fluorine and chlorine, $R^3$ represents hydrogen, fluorine, chlorine, bromine or represents methyl or ethyl, each of which is unsubstituted or substituted by a halogen selected from the group consisting of fluorine and chlorine, $R^4$ represents hydrogen, cyano, nitro, fluorine, chlorine or methoxy, $R^5$ represents hydrogen, hydroxyl, amino or represents methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, acetyl, propionyl, n- or i-butyroyl, acetylamino, propionylamino, methoxycarbonyl, ethoxycarbonyl, methylsulphonyl, ethylsulphonyl, n- or i-propylsulphonyl, n-, i-, s- or t-butylsulphonyl, methylsulphonylamino, ethylsulphonylamino, n- or i-propylsulphonylamino, n-, i-, s- or t-butylsulphonylamino, each of which is unsubstituted or substituted by cyano, fluorine, chlorine, methoxy or ethoxy, represents propenyl, butenyl, propenyloxy, butenyloxy, propinyl or butynyl, each of which is unsubstituted or substituted by a halogen selected from the group consisting of fluorine, chlorine and bromine, represents cyclopropyl, cyclobutyl, cyclopentyl, cyclohexyl, cyclopropylmethyl, cyclobutylmethyl, cyclopentylmethyl or cyclohexylmethyl, each of which is unsubstituted or substituted by a substituent selected from the group consisting of cyano, fluorine, chlorine, bromine, methyl and ethyl, represents phenyl, phenylamino, phenylcarbonylamino, phenylsulphonylamino, benzyl or phenylethyl, each of which is unsubstituted or substituted by a substituent selected from the group consisting of cyano, fluorine, chlorine, bromine, methyl, ethyl, n- and i-propyl, n-, i-, s- and t-butyl, difluoromethyl, trifluoromethyl, methoxy, ethoxy, n- and i-propoxy, difluoromethoxy, trifluoromethoxy, methylthio, ethylthio, difluoromethylthio, trifluoromethylthio, methylsulphinyl, ethylsulphinyl, methylsulphonyl and ethylsulphonyl, and $R^6$ represents hydrogen or represents methyl, ethyl, n- or i-propyl, propenyl, butenyl, propinyl or butinyl, each of which is unsubstituted or substituted by fluorine or chlorine, or together with $R^5$ represents ethane-1,2-diyl (dimethylene), propane-1,3-diyl (trimethylene), 2-oxa-propane-1,3-diyl, butane-1,4-diyl (tetramethylene), pentane-1,5-diyl or 3-oxa-pentane-1,5-diyl.

3. A process for preparing a substituted phenyluracil of the general formula (I)

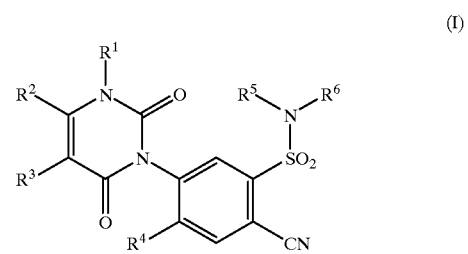

wherein $R^1$, $R^2$, $R^3$, $R^4$, $R^5$ and $R^6$ are each as defined in claim 1, comprising the step of reacting a chlorosulfonylphenyluracil of the general formula (II)

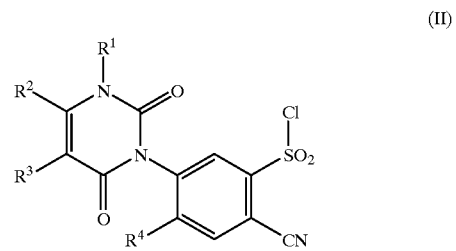

wherein $R^1$, $R^2$, $R^3$ and $R^4$ are each as defined above, with an amino compound of the general formula (III)

wherein $R^5$ and $R^6$ are each as defined above.

4. A herbicidal composition, comprising at least one substituted phenyluracil of the general formula (I) according to claim 1 and one or more extenders and/or surfactants.

5. A method for controlling undesirable plants, comprising the step of allowing a substituted phenyluracil of the general formula (I) according to claim 1 to act on undesirable plants and/or their habitat.

6. A process for preparing a herbicidal composition, comprising the step of mixing a substituted phenyluracil of the general formula (I) according to claim 1 with extenders and/or surfactants.

* * * * *